(12) United States Patent
Goto

(10) Patent No.: US 6,480,574 B2
(45) Date of Patent: Nov. 12, 2002

(54) X-RAY DIAGNOSTIC APPARATUS

(75) Inventor: Yasunori Goto, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/097,959

(22) Filed: Mar. 15, 2002

(65) Prior Publication Data

US 2002/0131557 A1 Sep. 19, 2002

(30) Foreign Application Priority Data

Mar. 16, 2001 (JP) ........................................ 2001-075962

(51) Int. Cl.[7] .................................................. G21K 1/00
(52) U.S. Cl. .......................................... 378/154; 378/62
(58) Field of Search ................................. 378/62, 154, 4

(56) References Cited

U.S. PATENT DOCUMENTS 5,812,629 A * 9/1998 Clauser ........................ 378/37
6,163,386 A * 12/2000 Kobayashi et al. .......... 348/304

FOREIGN PATENT DOCUMENTS

JP 11285486 * 10/1999

* cited by examiner

*Primary Examiner*—David P. Porta
*Assistant Examiner*—Pamela R. Hobden
(74) *Attorney, Agent, or Firm*—Oblon, Spivak, McClelland, Maier & Neustadt, P.C.

(57) ABSTRACT

An X-ray tube and an X-ray detector are supported by an arm in such a manner that a distance between the X-ray tube and an image reception plane of the X-ray detector can be changed. A grid is arranged on the image reception plane of the X-ray detector. The arm is supported by an arm support apparatus in such a manner that an angle of the arm can be changed. Moire image data files obtained by the grid are stored in a storage device in association with the distance between the X-ray tube and the image reception plane of the X-ray detector and the angle of the arm. Image data outputted from the X-ray detector is corrected by the moire correction circuit based on the moire image data selectively read from the storage device in accordance with the distance and the angle.

24 Claims, 9 Drawing Sheets

Correction data in these parts can not be collected

Correction data in these parts can not be collected

X-RAY DIAGNOSTIC APPARATUS

CROSS-REFERENCE TO RELATED APPLICATIONS

This application is based upon and claims the benefit of priority from the prior Japanese Patent Application No. 2001-075962, filed Mar. 16, 2001, the entire contents of which are incorporated herein by reference.

BACKGROUND OF THE INVENTION

1. Field of the Invention

The present invention relates to an X-ray diagnostic apparatus capable of changing an angle of radiography.

2. Description of the Related Art

In an X-ray diagnostic apparatus, an X-ray grid for eliminating a scattered ray is usually arranged in an image reception plane of an image intensifier or a flat panel type X-ray detector. The X-ray grid is constituted by assembling many laminated plates of metal or the like in the form of a grid or in parallel. In the prior art, since a gap between the grid plates (which will be referred to as grid density hereinafter) is relatively smaller than the solution of a radiographic system, the moire does not appear in an image as an artifact.

However, with recent increase in the resolution of the radiographic system, the grid appears in an image as the moire-like artifact.

Of course, the moire can be seemingly dissolved in principle by narrowing the grid density so that the radiographic system can not recognize it. However, the grid density is configured by the order of several tens per 1 cm even now, and the X-ray grid can not be constituted with the narrower density. Even if the X-ray grid can be constituted with the narrower density, the manufacturing cost becomes too high. Therefore, solving this problem by processing the grid is not realistic.

Further, for example, Jpn. Pat. Appln. KOKAI Publication No. 11-146277 discloses elimination of the moire by image processing. That is, when an image of a uniform phantom is taken in place of a patient, moire image data is basically obtained, and elimination of the moire can be realized by actually subtracting the moire image data from patient image data.

This moire elimination method, however, can not be applied to X-ray diagnosis of the circulatory system or the like in some cases. The paramount reason is that the pattern of moire fringes varies in many ways depending on a radiographic angle or an SID (Source Image Distance), for example.

BRIEF SUMMARY OF THE INVENTION

It is an object of the present invention is to improve the moire correction accuracy in an X-ray diagnostic apparatus.

According to a first aspect of the present invention, there is provided an X-ray diagnostic apparatus comprising: an X-ray tube; an X-ray detector; a grid arranged on an image reception plane of the X-ray detector; an arm which supports the X-ray tube and the X-ray detector in such a manner that a distance between the X-ray tube and the image reception plane of the X-ray detector can be changed; an arm support device which supports the arm in such a manner that an angle of the arm can be changed; a storage device which stores files of moire image data obtained by the grid in association with at least one of the distance and the angle; and a moire correction circuit which corrects image data outputted from the X-ray detector based on moire image data selectively read from the storage device in accordance with at least one of the distance and the angle from the storage device.

According to a second aspect of the present invention, there is provided an X-ray diagnostic apparatus comprising: an X-ray tube; an X-ray detector; a grid arranged on an image reception plane of the X-ray detector; an arm which supports the X-ray tube and the X-ray detector in such a manner that a distance between the X-ray tube and the image reception plane can be changed; an arm support device which supports the arm in such a manner that an angle of the arm can be changed; a moire correction data generation circuit which performs frequency analysis of image data outputted from the X-ray detector, specifies a spatial frequency corresponding to a moire pattern and generates moire correction data based on the specified spatial frequency; and a moire correction circuit which corrects image data outputted from the X-ray detector based on the generated moire correction data.

According to a third aspect of the present invention, there is provided an X-ray diagnostic apparatus comprising: an X-ray tube; an X-ray detector; a grid arranged on an image reception plane of the X-ray detector; an arm which supports the X-ray tube and the X-ray detector in such a manner that a distance between the X-ray tube and the image reception plane of the X-ray detector can be changed; an arm support device which supports the arm in such a manner that an angle of the arm can be changed; a frequency analysis circuit which is configured to perform frequency analysis of image data outputted from the X-ray detector and specify a spatial frequency corresponding to a moire pattern; and a moire correction circuit which is configured to attenuate specified spatial frequency component of the image data outputted from the X-ray detector.

According to a fourth aspect of the present invention, there is provided an X-ray diagnostic apparatus comprising: an X-ray tube; an X-ray detector; a grid arranged on an image reception plane of the X-ray detector; an arm which supports the X-ray tube and the X-ray detector in such a manner that a distance between the X-ray tube and the image reception plane of the X-ray detector can be changed; a sensor which detects a distance between the X-ray tube and the image reception plane of the X-ray detector; an arm support device which supports the arm in such a manner that an angle of the arm can be changed; a storage device which stores moire image data when the distance between the X-ray tube and the image reception plane of the X-ray detector is a reference distance; a moire image enlargement circuit which is configured to enlarge the moire image data based on the distance detected by the sensor and the reference distance; and a moire correction circuit which corrects the image data outputted from the X-ray detector based on the enlarged moire image data.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An X-ray diagnostic apparatus according to the present invention will now be described based on an embodiment.

Figure 1:
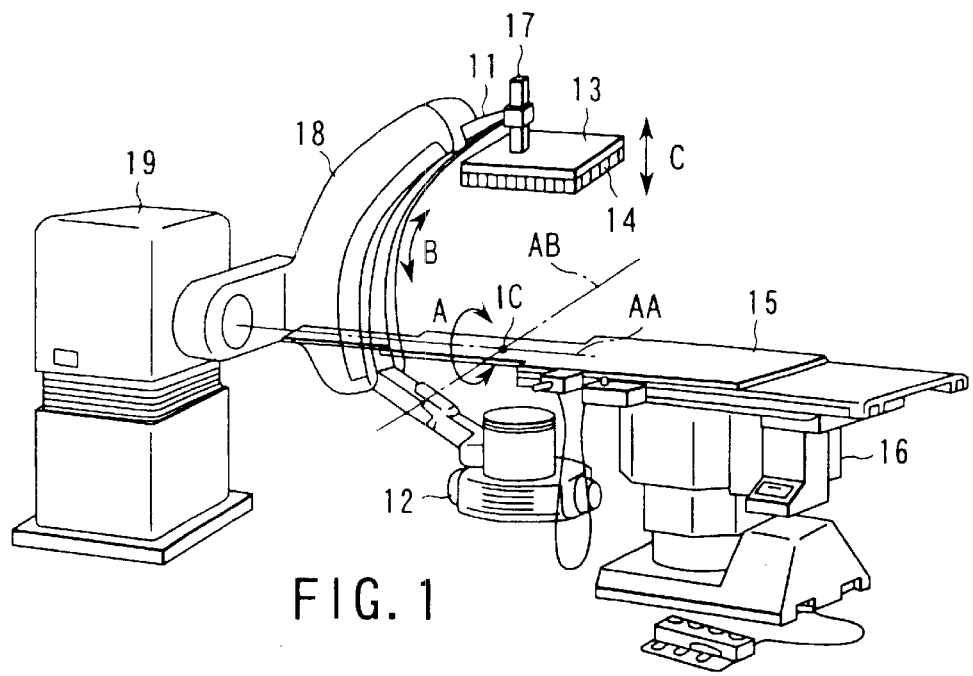
FIG. 1 is a structural view showing a trestle of an X-ray diagnostic apparatus according to an embodiment of the present invention.

FIG. 1 is a structural view showing a trestle of an X-ray diagnostic apparatus according to this embodiment. An X-ray tube 12 is mounted at one end of a C-shaped or U-shaped arm 11. A flat panel type detector (flat panel detector) 13 is mounted at the other end of the arm 11 in a direction opposed to the X-ray tube 12. A movement mechanism 17 movably supports the flat panel type detector 13 in the front-and-back direction. Movement of the flat panel type detector 13 changes a distance SID (Source Image Distance) between an image reception plane of the flat panel type detector 13 and the X-ray tube 12.

An indirect conversion type or a direct conversion type is adopted for the flat panel type detector 13. The flat panel type detector 13 which is of the indirect conversion type includes a scintillator plate which converts an incoming X ray into light and a photodiode array which converts this light into an electrical signal (electric charge). The flat panel type detector 13 which is of the direct conversion type has a semiconductor element array using, e.g., selenium or cadmium as an X-ray sensitive material. The image reception plane of the flat panel type detector 13 is defined as a surface of the scintillator plate or the semiconductor element array.

An X-ray grid 14 is arranged on the image reception plane of the flat panel type detector 13. The X-ray grid 14 has a plurality of thin lead plates arranged in the form of a grid or in parallel (grid plates) in order to mainly eliminate a scattered ray which obliquely enters the image reception plane at a predetermined angle or a larger angle.

The arm 11 is supported by an arm holder 18 so as to be capable of slidingly rotating in a direction indicated by an arrow B. The arm holder 18 is supported by a holder base 19, which is provided on a floor or suspended from the ceiling, so as to be capable of axially rotating in a direction indicated by an arrow A. Typically, a rotation axis AA of the arrow A and a rotation axis AB of the arrow B are orthogonal to each other at a fixed point called an isocentre IC.

Incidentally, assuming that a position at which the flat panel type detector 13 is at the top is a reference position, an angle of the arm 11 in the direction of the arrow A from the reference position is notated as θA, and an angle of the arm 11 in the direction of the arrow B from the reference position is noted as θB.

A top plate 15 on which a patient P is mounted is arranged between the X-ray tube 12 and the flat panel type detector 13. This top plate 15 is supported by a top plate base 16 so as to be capable of moving in the vertical and horizontal directions.

Figure 2:
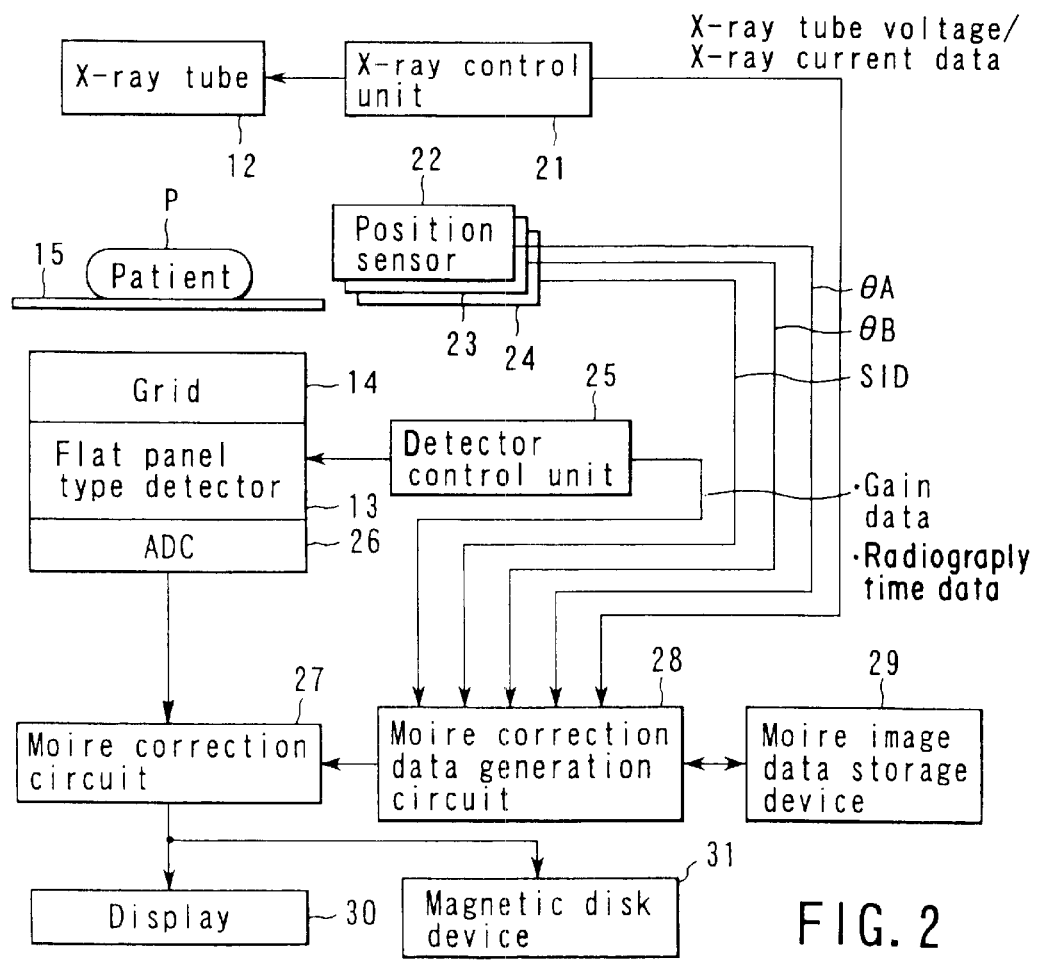
FIG. 2 is a block diagram showing primary parts of the X-ray diagnostic apparatus according to the embodiment.

FIG. 2 is a block diagram showing primary pars of the apparatus according to this embodiment. An X-ray control unit 21 generates a high voltage (X-ray tube voltage) to be applied between electrodes of the X-ray tube 12. Furthermore, the X-ray control unit 21 generates a filament current for heating filaments of the X-ray tube 12. Generally, the radiation quality of an X ray varies in accordance with the X-ray tube voltage. The intensity of an X ray varies in accordance with the X-ray tube current. The X-ray tube current relates to the filament current. The X-ray control unit 21 supplies X-ray tube voltage data, X-ray tube current data and radiography time data to a moire correction data generation circuit 28.

In order to detect the angle θA, the angle θB and the distance SID, position sensors 22, 23 and 24 are attached to the arm 18. The position sensors 22, 23 and 24 are typically rotary encoders. Angle data θA and θB and SID data detected by the position sensors 22, 23 and 24 are supplied to the moire correction data generation circuit 28.

A detector control unit 25 mainly controls storage of electric charge of the flat panel type X-ray detector 13, reading of signals, and a gain of a preamplifier incorporated in the flat panel type X-ray detector 13. The gain data is supplied to the moire correction data generation circuit 28.

Figure 3:
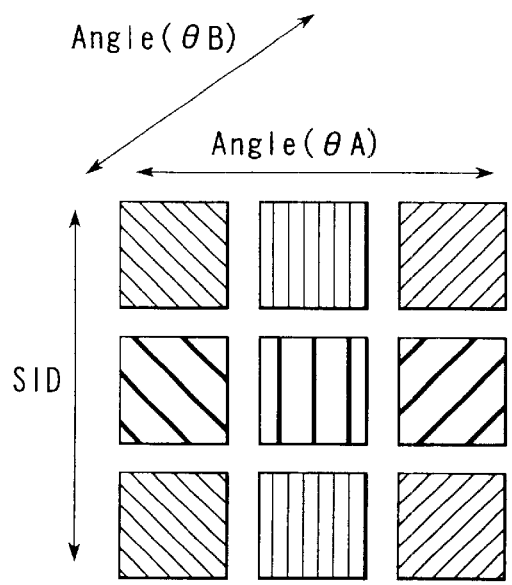
FIG. 3 is a view showing an example of moire image data stored in a moire image data storage device illustrated in FIG. 2.

An output signal from the flat panel type X-ray detector 13 is converted into a digital signal by an analog-to-digital converter (ADC) 26, and supplied to a moire correction circuit 27 as image data as shown in FIG. 3. Incidentally, as image data described in the following, there are roughly two types, i.e., image data obtained by an radiographic operation when a patient P which is a target of an actual examination is arranged between the X-ray tube 12 and the detector 13 and image data obtained by an radiographic operation when the patient is not arranged between the X-ray tube 12 and the detector 13. The former is called original image data. The latter image data is called moire image data since moire fringes caused mainly due to an error in manufacture of the grid 14 come out in this image data.

The moire correction circuit 27 corrects the original image data based on moire correction data supplied from the moire correction data generation circuit 28. The corrected original image data is outputted to a display 30 and a magnetic disk device 31, displayed and recorded.

A moire image data storage device 29 stores a plurality of moire image data files as shown in FIG. 3. In order to generate a moire image data file, the radiographic operation is carried out without providing the top plate 15 and the patient P between the X-ray tube 12 and the flat panel type detector 13. As a result, it is possible to obtain an image data file in which moire fringes due to the X-ray grid 14 mainly come out (moire image data file). The radiographic operation for generating the moire image data file is repeatedly carried out while changing at least one of the angle θA, the angle θB and the distance SID. The status when taking the moire image, namely, angle data θA, angle data θB and SID data are associated with each moire image data file. In data associated with a plurality of the moire image data files, at least one of the angle θA, the angle θB and the distance SID is different from that of other data.

Figure 4A:
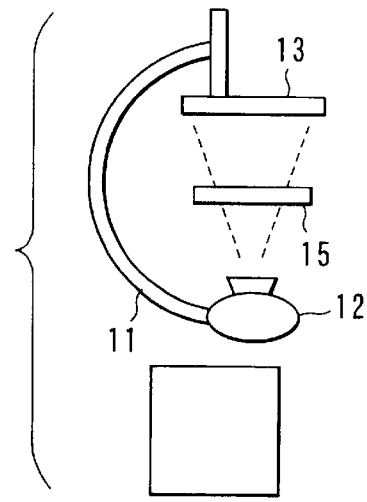
FIGS. 4A, 4B and 4C are explanatory views showing a prior art radiographic method for moire image data.
Figure 4B:
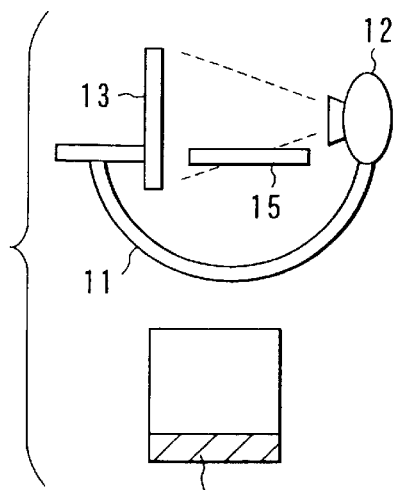
Figure 4C:
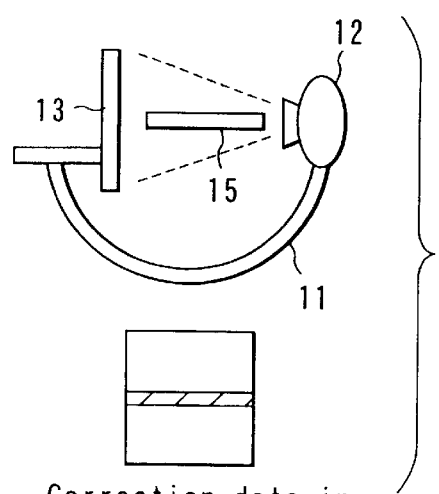

Incidentally, in the prior art, the radiographic operation for obtaining the moire image data is carried out with the top plate 15 intervening between the X-ray tube 12 and the detector 13 as shown in FIG. 4A. In this state, as shown in FIGS. 4B and 4C, a shadow of the top plate 15 disadvantageously comes out in the moire image data. Moire correction is impossible in the part of this shadow. In this embodiment, in order to avoid this problem, the radiography for obtaining the moire image data is performed without arranging the top plate 15 and the patient P between the X-ray tube 12 and the detector 13, or with a phantom such as copper plate being attached to a tube irradiation opening and without providing the top plate 15 and the patient P between the X-ray tube 12 and the detector 13.

Figure 5A:
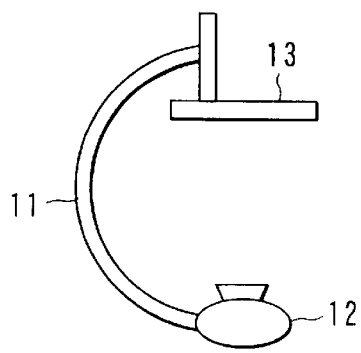
FIGS. 5A, 5B and 5C are explanatory views showing a radiographic method for moire image data depicted in FIG. 3.
Figure 5B:
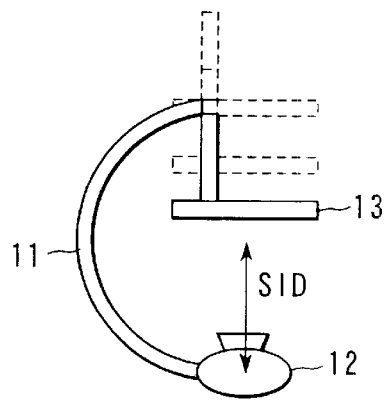
Figure 5C:
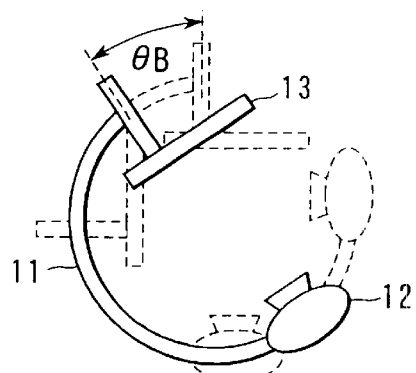

Furthermore, the radiographic operation for obtaining such moire image data is repeated in various states such that the angle θA and the angle θB are provided at the reference positions (both are zero degree) as shown in FIG. 5A and that the distance SID is the reference distance as well as that at least one of the angle θA, the angle θB and the distance SID deviates from the reference. As a result, there can be obtained not only the moire image data corresponding to the reference position but also a plurality of the moire image data files having at least one of the angle θA, the angle θB and the distance SID being slightly different from the reference position.

When the angle θA and/or the angle θB is deviated from the reference position, namely, when the arm 11 is inclined in either or both of the directions A and B, the arm 11 is distorted by weights of the arm 11, the X-ray tube 12 and the detector 13. Distortion of the arm 11 inclines or distorts the moire fringes. Moreover, when the distance SID is changed to be shorter or longer than the reference distance, the magnification of an image varies. When the magnification changes, an interval of the moire fringes varies. That is, when at least one of the angle θA, the angle θB and the distance SID changes, the appearance pattern of the moire fringes varies.

Therefore, a plurality of moire image data files having at least one of the angle θA, the angle θB and the distance SID being different are obtained in advance, and the original image data is corrected by using the moire image data files obtained in the state which is the same as or similar to the angle θA, the angle θB and the distance SID in the actual radiography. As a result, the moire correction accuracy can be improved.

Of course, the moire image data file obtained in the state which is the same as the angle θA, the angle θB and the distance SID in the actual radiography may not be stored in the moire image data storage device 29 in some cases. In such a case, the moire correction data generation circuit 28 selects one moire image data file obtained in the state which is closest to the angle θA, the angle θB and the distance SID in the actual radiography. Alternatively, in the moire correction data generation circuit 28, two or more moire image data files obtained in the state closest to the angle θA, the angle θB and the distance SID in the actual radiography may be read from the moire image data storage device 29, and the moire image data file corresponding to the angle θA, the angle θB and the distance SID in the actual radiography may be obtained from a plurality of these moire image data files by the distance-linear interpolation.

In the radiography state for obtaining the moire image data file, the gain, the X-ray tube voltage, the X-ray tube current and the radiography time are fixed to respective reference values. The moire correction data generation circuit 28 generates the moire correction data by correcting the contrast of the moire image data file selectively read from the storage device 29 or the moire image data file obtained by interpolation based on the actual gain, the X-ray tube voltage, the X-ray tube current and the radiography time.

Incidentally, although the moire image data is stored in the storage device 29, the moire correction data created by the moire correction data generation circuit 28 may be stored in association with the angles, the distance as well as the X-ray tube voltage and the X-ray tube current, and the moire correction data may be reused when radiography is carried out in the same state.

This moire correction data is supplied to the moire correction circuit 27. The original image data is corrected in the moire correction circuit 27 in accordance with the moire correction data. Actually, addition, subtraction, multiplication or division of the moire correction data are performed with respect to the original image data, or the original image data is subjected to logarithmic transformation or index transformation in accordance with the moire correction data. Any calculation method can be arbitrary applied to this correction. Here, subtraction is taken as an example for explanation.

It is to be noted that moire correction data generation processing and moire correction processing can be realized by hardware or software.

As described above, the moire correction accuracy can be improved by generating the moire image data without providing the top plate, independently using the moire image data in accordance with the angles θA and θB of the arm and the distance SID, and correcting the moire image data in accordance with the gain, the X-ray tube current, the X-ray tube voltage and the radiography time in order to create the correction data.

Figure 6:
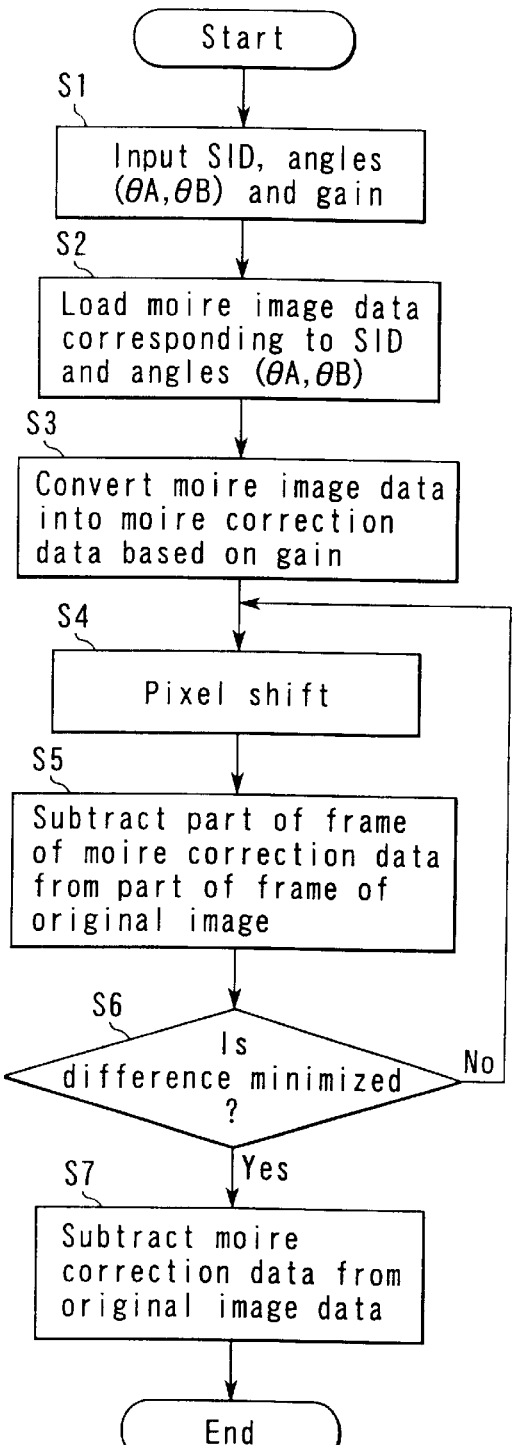
FIG. 6 is a flowchart showing a first correction procedure in the embodiment.

FIG. 6 shows the procedure of moire correction processing according to this embodiment. At S1, to the moire correction data generation circuit 28 are first supplied each set of data of the angle θA, the angle θB, the distance SID and the gain when performing radiography to the patient from the sensors 22, 23 and 24, information of the X-ray tube voltage and the X-ray tube current and the radiography time from the X-ray control unit 21, and the gain data from the detector control unit 25. The moire correction data generation circuit 28 selectively reads the moire image data associated with the angle θA, the angle θB and the distance SID supplied thereto from the image data storage device 29 (S2)

The moire correction data generation circuit 28 converts the read moire image data into the moire correction data based on the X-ray tube voltage data, the X-ray tube current data, the radiography time and the gain data (S3). As a result, the concentration of the moire fringes in the moire image data is caused to become equivalent to or approximate to the concentration of the moire fringes in the original image data.

Figure 7:
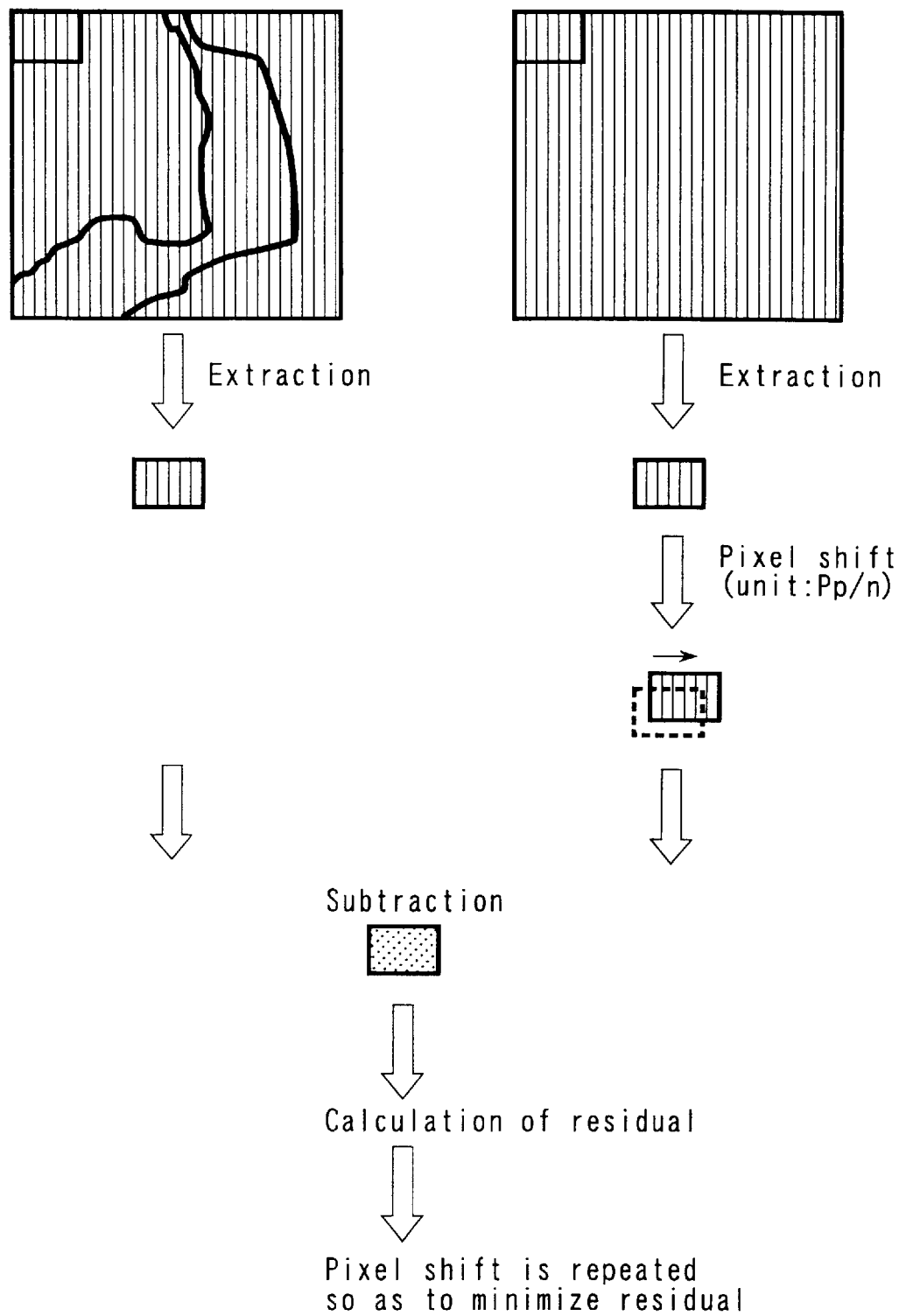
FIG. 7 is a conceptual view showing processing at S4, S5 and S6 of FIG. 6 in the embodiment.

Subsequently, in order to correct the spatial displacement of the moire correction data from the original image data, pixel shift processing (S4), subtraction processing (S5) and minimization judgment processing (S6) are executed in loop. FIG. 7 typically shows its concept. At first, a partial area in the frame, for example a partial area at the same corner, is extracted from the original image data and the moire correction data. Then, the position of the partial area of the moire correction data is shifted in the direction vertical to the moire fringes with Pp/n being determined as a unit distance. Pp is a pitch of adjacent pixels (for example, a distance between central points), and n is an arbitrary positive integer for determining the accuracy for correcting the displacement.

Subtraction is performed between the shifted partial area of the moire correction data and the partial area of the original image data, and a residual sum total is calculated. In order to minimize the residual sum total, pixel shift (S4) and subtraction (S5) are repeated while increasing the shift distance in accordance with the unit distance Pp/n. The shift distance of the partial area of the more correction data when the residual sum total is minimized represents the spatial displacement of the moire correction data with respect to the original image data.

In accordance with the thus obtained spatial displacement between the original image data and the moire correction data, one or both of the positions of the partial areas are shifted and subtraction is executed (S7). As a result, the moire fringes can be eliminated or reduced from the original image data.

Incidentally, examination radiography may be effected with the grid 14 being removed in some cases. In such a case, moire correction processing is not required. Specifically, in this case, the original image data substantially passes through the moire correction circuit 27 and is supplied to the display 30. Substantially passing means that the original image data is directly supplied to the display 30 from the ADC 26 through the moire correction circuit 27 or the correction data from which the correction effect is eliminated is used to correct the original image data in the moire correction circuit 27.

Figure 8:
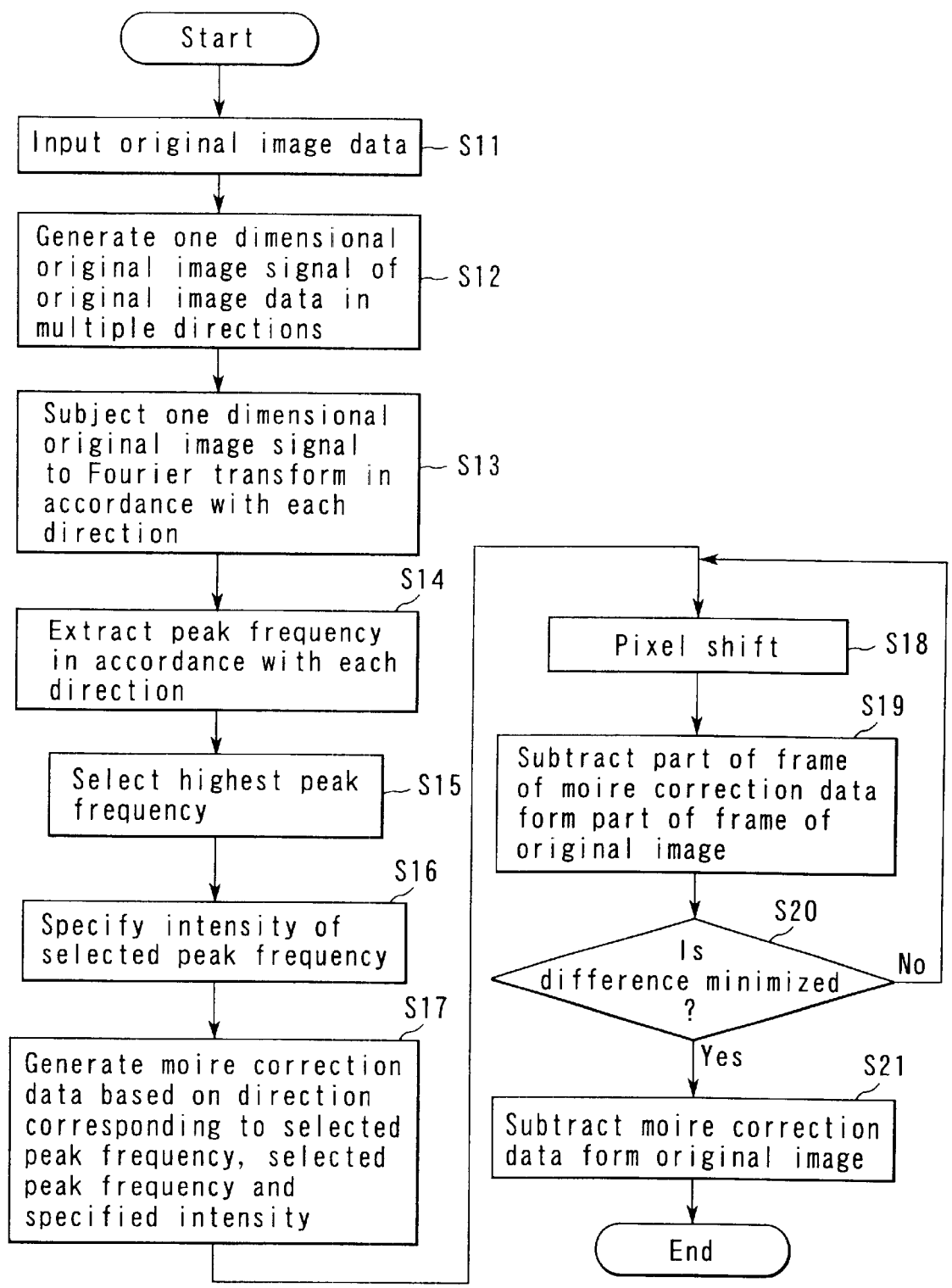
FIG. 8 is a flowchart showing a second correction procedure in the embodiment.
Figure 9A:
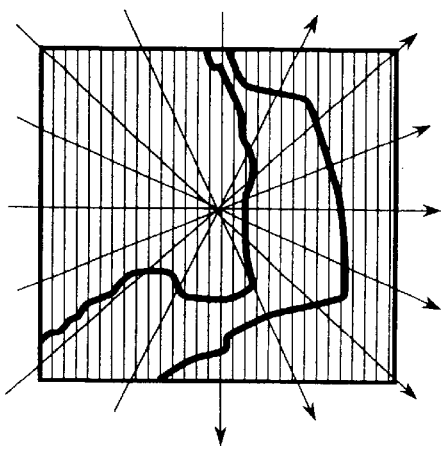
FIGS. 9A, 9B, 9C and 9D are views showing a direction of generation of a one dimensional original image signal illustrated in FIG. 8.
Figure 9B:
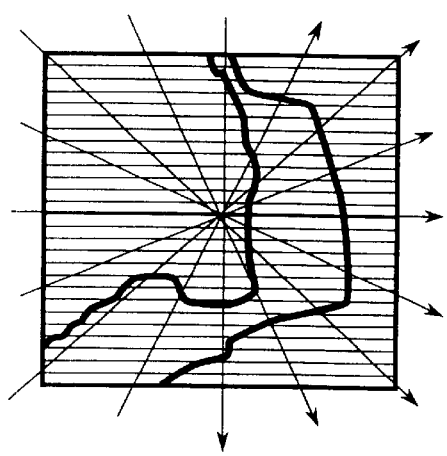
Figure 9C:
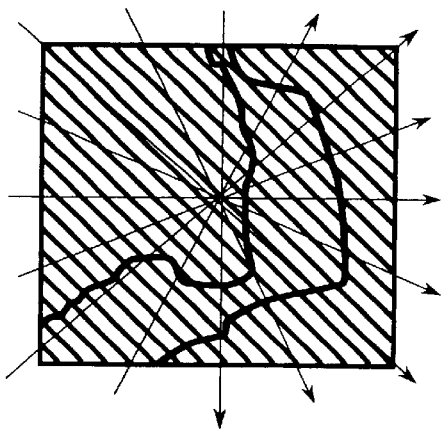
Figure 9D:
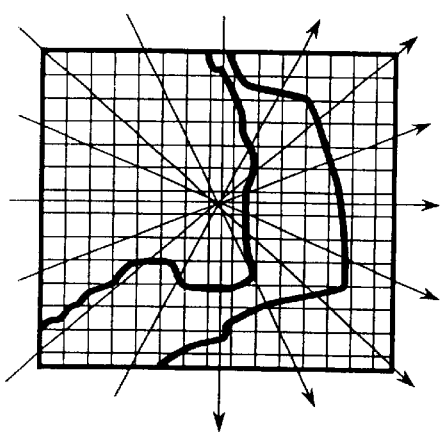

FIG. 8 shows the procedure of another moire correction processing. The moire correction processing described in connection with FIG. 6 can be substituted by both of moire correction processing shown in FIG. 8 and later-described moire correction processing shown in FIGS. 12 and 13. In addition, the moire correction data generation circuit 28 and the moire correction circuit 27 may be constituted so that arbitrary two, three, four or five techniques in FIGS. 6, 8, 12, 13 and 14 can be carried out, and an operator may selectively apply any desired technique. Additionally, arbitrary two, three for four techniques or all of five techniques in FIGS. 6, 8, 12, 13 and 14 may be automatically applied to the original image data, and an operator may select an image obtained by the technique having the best moire reduction effect.

As shown in FIG. 8, the original image data is supplied to the moire correction data generation circuit 28 from the ADC 26 (S11). As shown in FIGS. 9A, 9B, 9C and 9D, the moire correction data generation circuit 28 generates a plurality of one dimensional original image signals corresponding to a plurality of directions from the original image data (S12). A purpose of generating a plurality of one dimensional original image signals in a plurality of directions is to specify a direction of the moire fringes.

Subsequently, the moire correction data generation circuit 28 respectively subjects a plurality of the one dimensional original image signals to Fourier transform (S13). As Fourier transform, either fast Fourier transform FFT or discrete Fourier transform can be adopted. The moire correction data generation circuit 28 may subjects to the original image data two dimensional (2D) FFT.

Figure 10:
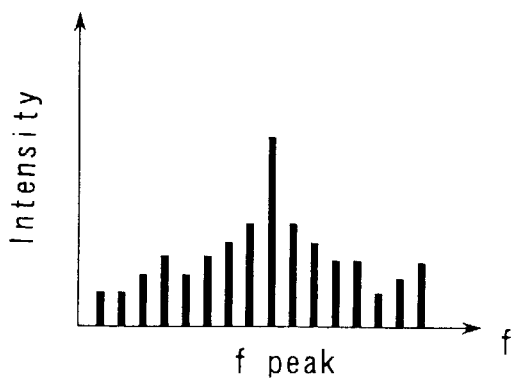
FIG. 10 is a view showing an example of a frequency spectrum of the one dimensional original image signal obtained by Fourier transform depicted in FIG. 8.

By executing Fourier transform, a plurality of frequency distributions respectively corresponding to a plurality of one dimensional original image signals in different directions are generated as shown in FIG. 10. Then, a frequency corresponding to the moire fringes, for example a peak frequency having the highest intensity, is extracted from a predetermined band of each frequency distribution (S14). The predetermined band can be estimated based on a grid plate pitch. The highest peak frequency is selected from a plurality of peak frequencies in different directions (S15), and the intensity of the selected highest peak frequency component is specified (S16). The direction corresponding to the selected highest peak frequency corresponds to a direction vertical to the moire fringes.

Figure 11:
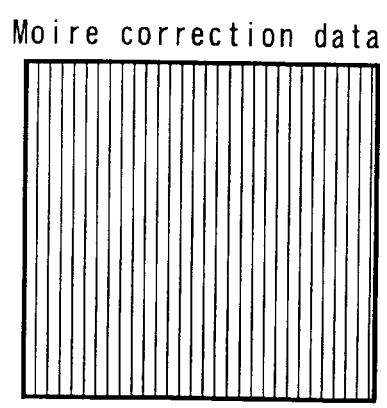
FIG. 11 is a view showing generated moire correction data illustrated in FIG. 8.

The moire correction data generation circuit 28 forms a plurality of moire fringes in parallel with a cycle of an inverse number of the selected highest peak frequency in accordance with the direction corresponding to the selected highest peak frequency, and generates moire correction data shown in FIG. 11 by setting the concentration of the moire fringes in accordance with the intensity of the peak frequency component (S17).

The displacement of the generated moire correction data with respect to the original image data is obtained at S18, S19 and S20 similarly at S4, S5 and S6, and one or both of data are shifted in accordance with the displacement and subtraction is performed (S21). As a result, the moire fringes can be eliminated or reduced from the original image data.

In the method illustrated in FIG. 8, the moire correction data is generated in the moire correction data generation circuit 28 based on the direction corresponding to the selected highest peak frequency, the selected highest peak frequency and the intensity of the peak frequency component. However, it is also possible to create a plurality of moire standard image data files having different directions and spatial frequencies and the standard concentration, store them in the data storage device 29 in advance, selectively read from the data storage device 29 into the moire correction data generation circuit 28 the moire standard image data file corresponding to the highest peak frequency, which is obtained based on the actual original image data at S15, and its direction from a plurality of the moire standard image data files as indicated at S22 in FIG. 12, set the concentration of the moire fringes in the read moire standard image data in accordance with the intensity specified at S16, thereby generating the moire correction data.

Figure 13:
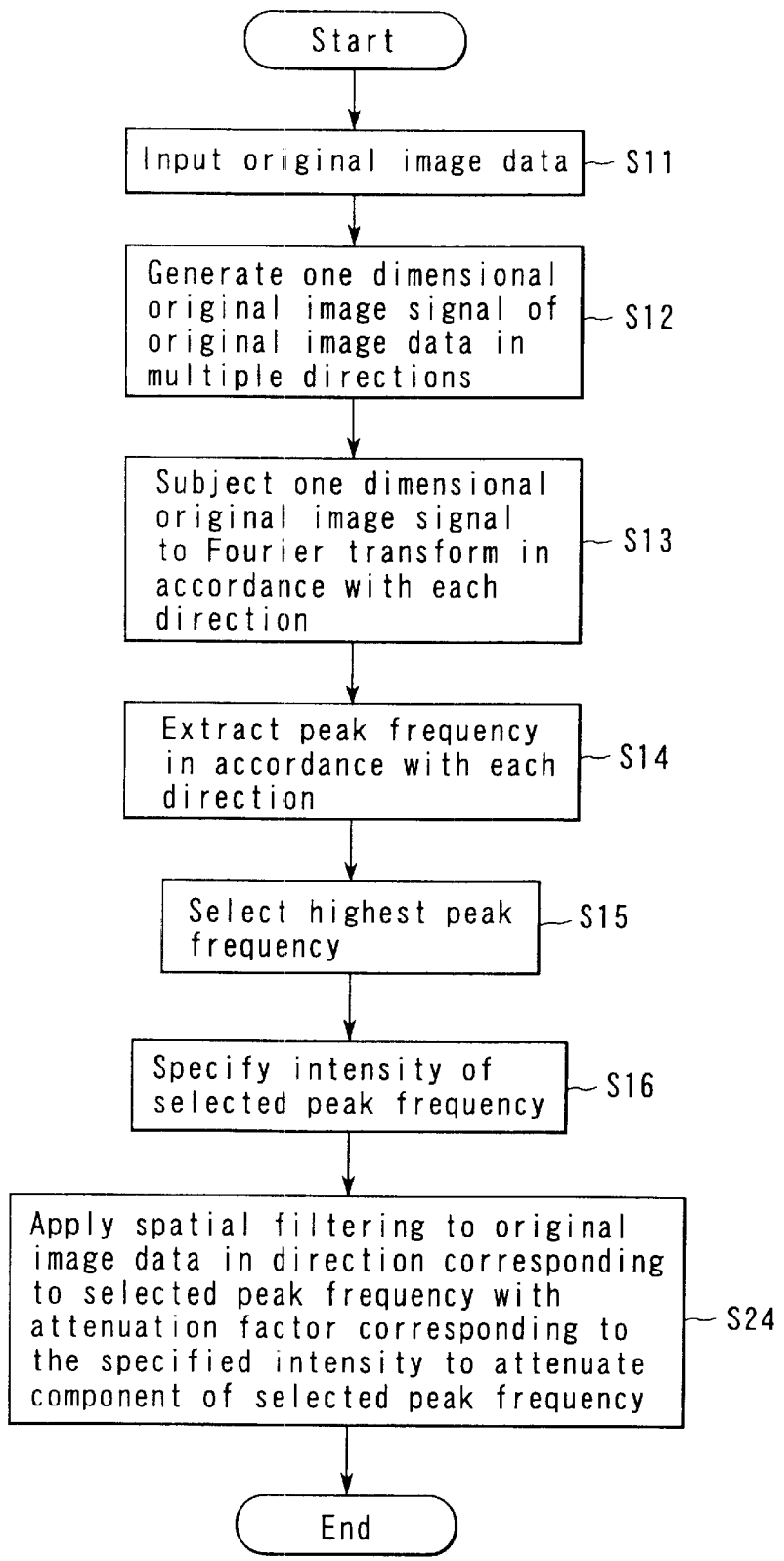
FIG. 13 is a flowchart showing a fourth correction procedure in the embodiment.

The technique shown in FIG. 13 is a technique which does not require the moire image data and the moire standard image data. At S15, the highest peak frequency and its direction are obtained from the actual original image data. This peak frequency indicates a spatial frequency of the moire fringes. Therefore, at S24, the original image data is subjected to spatial filtering by the correction circuit 27 in such a manner that the spatial frequency component of the peak frequency is attenuated in the obtained direction with an attenuation factor corresponding to the contrast or density specified at S16. Spatial filtering can be realized by both software and hardware (general digital filter which is of FIR or IIR type), and a coefficient train according to the direction, the peak frequency and the attenuation factor is given to a filtering program code or a digital filter.

Figure 12:
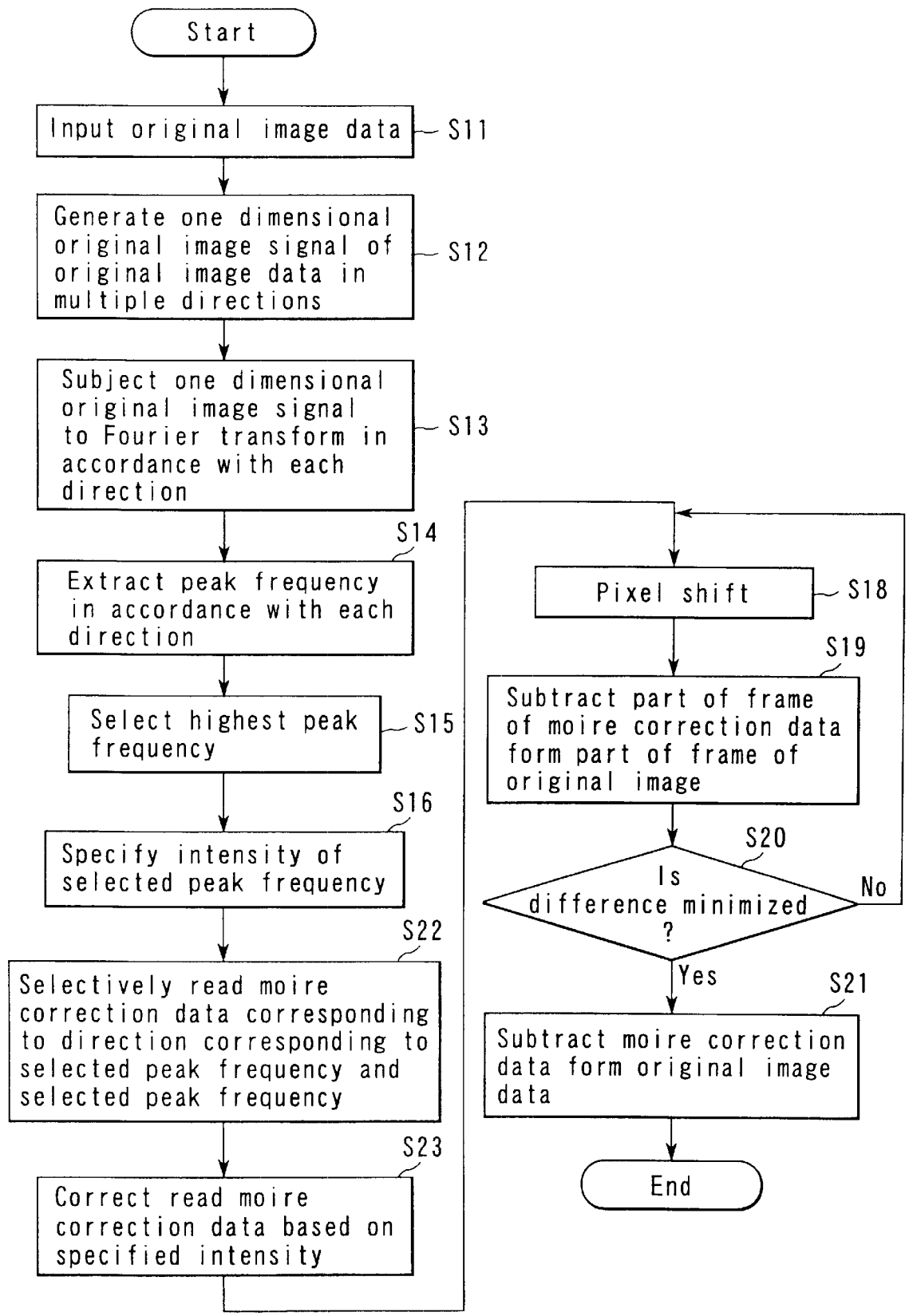
FIG. 12 is a flowchart showing a third correction procedure in the embodiment.
Figure 14:
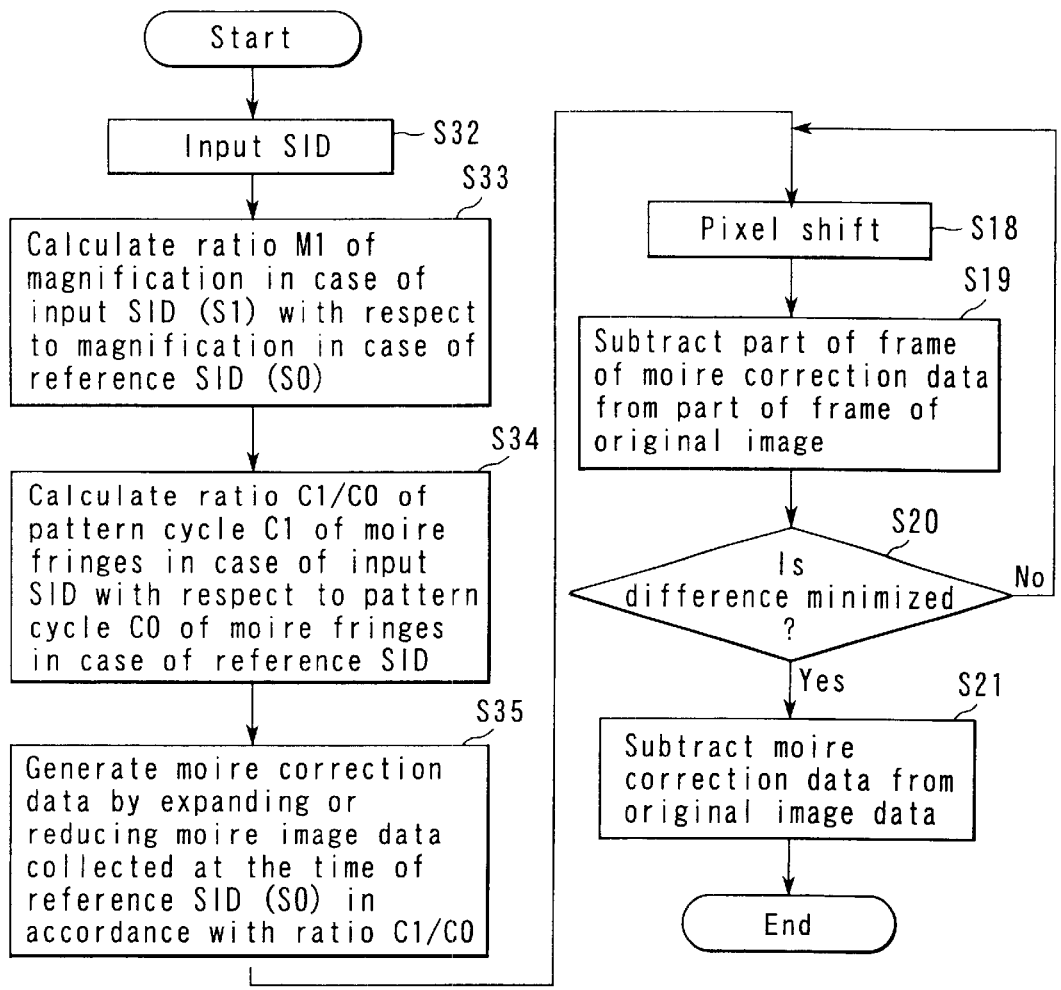
FIG. 14 is a flowchart showing a fifth correction procedure in the embodiment.

In the above-described techniques illustrated in FIGS. 6, 8 and 12, a plurality of moire image data files or moire standard image data files respectively corresponding to a plurality of distances SID must be prepared in advance. Further, data files with various angles are required for the respective distances SID, and a number of these files becomes very large in some cases. FIG. 14 shows a technique for reducing a number of the files. This technique generates the moire correction data corresponding to the original image data by correcting the moire image data corresponding to the reference SID in accordance with SID at the time of actual examination radiography. Although the angle is actually different, a plurality of moire image data files or moire standard image data files with the distance SID being a reference value and constant are prepared, and a file corresponding to an actual angle is selectively used among these files.

SID data at the time of actual examination radiography is first supplied from the sensor 24 to the moire correction data generation circuit 28 (S32). Here, although the grid 14 is attached on the image reception plane of the detector 13, a margin unavoidable in the structure or in the assembling process exists between the grid 14 and the image reception plane of the detector 13. That is, the grid 14 is slightly distanced from the image reception plane of the detector 13. Therefore, a pattern cycle of the moire fringes varies in accordance with a change in SID.

Here, a ratio of the pattern cycle of the moire fringes corresponding to the actual SID relative to the pattern cycle of the moire fringes corresponding to the reference SID is obtained, and the moire correction data is generated by expanding or reducing the moire image data file with the reference SID in a direction vertical to the moire fringes in accordance with the ratio.

At S33, a ratio M1 of the magnification of a grid projected image on the image reception plane of the detector with respect to an entity of the grid 14 when SID is a reference value S0 relative to the magnification of a grid projected image on the image reception plane of the detector with respect to the entity of the grid 14 when SID is an actual value S1 is first calculated based on the expression (1):

$$M1=(S1/(S1-D0)/(S0/(S0-D0))) \quad (1)$$

It is to be noted that D0 indicates a physical distance between the grid 14 and the image reception plane of the detector.

A ratio (C1/C0) of a pattern cycle C0 of the moire fringes when SID=S0 relative to a pattern cycle C1 of the moire fringes when SID=S1 is then calculated (S34). The pattern cycle C0 of the moire fringes when SID=S0 can be obtained by the following expression:

$$C0=(Pg/(Pp-Pg))\times Pp \quad (2)$$

Figure 15:
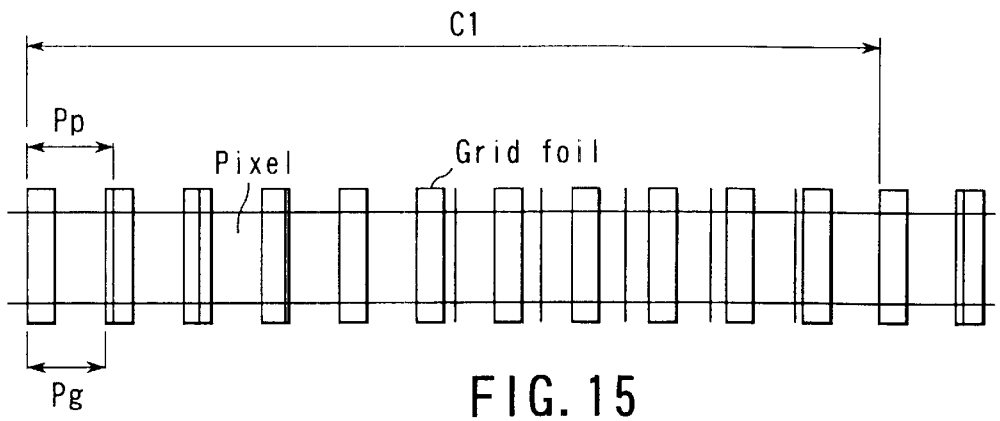
FIG. 15 is a supplementary view of FIG. 14.

It is to be noted that, as shown in FIG. 15, Pp indicates a pixel pitch (actual size) of the detector 13 and Pg represents a pitch of a projected image of the grid plate (lead foil) of the grid 13 when it is projected on the image reception plane of the detector 13 when SID=S0. That is, the moire fringes are generated due to an error in manufacture of the pitch Pg of the grid plate projected image on the image reception plane with respect to the actual pixel pitch Pp of the detector 13, and the displacement of the grid plate projected image accumulatively increases with respect to the pixel in units of the error (Pp−Pg).

Here, when SID=S1, the pitch of the grid plate projected image on the image reception plane can be obtained by the following expression:

$$Pg \times M1$$

Therefore, the pattern cycle C1 of the moire fringes when SID=S1 can be obtained by the following expression:

$$C1=((Pg \times M1)/(Pp-(Pg \times M1)))\times Pp \quad (3)$$

Based on the expressions (2) and (3), the following calculation is performed at S34:

$$C1/C0=(Pp-Pg)/((Pp/M1)-Pg) \quad (4)$$

The moire image data with the reference SID (S0) is enlarged in one direction vertical to the moire fringes in accordance with the ratio C1/C0 of the thus calculated pattern cycle (S35). As a result, the moire correction data is generated.

The displacement of the generated moire correction data with respect to the original image data is obtained at S18, S19 and S20 similarly at S4, S5 and S6, and one or both of data are shifted in accordance with the displacement and subtraction is carried out (S21). Consequently, the moire fringes can be eliminated or reduced from the original image data.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnostic apparatus comprising:
    an X-ray tube;
    an X-ray detector;
    a grid arranged on an image reception plane of said X-ray detector;
    an arm configured to support said X-ray tube and said X-ray detector in such a manner that a distance between said X-ray tube and said image reception plane of said X-ray detector can be changed;
    an arm support device configured to support said arm in such a manner that an angle of said arm can be changed;
    a storage device configured to store moire image data files including moire fringes by said grid in association with at least one of said distance and said angle; and
    a moire correction circuit configured to correct image data outputted from said X-ray detector based on moire image data file selectively read from said storage device in accordance with at least one of said distance and said angle.

2. The X-ray diagnostic apparatus according to claim 1, wherein said X-ray detector is a flat panel type detector adopting a direct conversion system or an indirect conversion system.

3. The X-ray diagnostic apparatus according to claim 1, further comprising a circuit configured to adjust the contrast or density of said moire image data selectively read from said storage device based on at least one of an X-ray tube voltage, an X-ray tube current of said X-ray tube, a gain of said X-ray detector and a radiography time.

4. The X-ray diagnostic apparatus according to claim 1, further comprising a circuit configured to dissolve or reduce the displacement of said moire image data selective read from said storage device with respect to image data outputted from said X-ray detector.

5. The X-ray diagnostic apparatus according to claim 1, wherein the moire image data files are obtained in a condition no top plate for mounting a patient is arranged between said X-ray tube and said X-ray detector.

6. The X-ray diagnostic apparatus according to claim 1, further comprising a circuit configured to generate a new moire image data file from moire image data files read from said storage device by a distance-linear interpolation.

7. The X-ray diagnostic apparatus according to claim 1, wherein when an examination radiography is effected with the grid being removed, said image data outputted from said X-ray detector substantially passes through said moire correction circuit.

8. An X-ray diagnostic apparatus comprising:
an X-ray tube;
an X-ray detector;
a gird arranged on an image reception plane of said X-ray detector;
an arm configured to support said X-ray tube and said X-ray detector in such a manner that a distance between said X-ray tube and said image reception plane of said X-ray detector can be changed;
an arm support device configured to support said arm in such a manner that an angle of said arm can be changed;
a moire correction data generation circuit configured to perform frequency analysis of image data outputted from said X-ray detector, specifies a spatial frequency corresponding to a moire pattern, and generates moire correction data based on said specified spatial frequency; and
a moire correction circuit configured to correct image data outputted from said X-ray detector based on said generated moire correction data.

9. The X-ray diagnostic apparatus according to claim 8, wherein the spatial frequency corresponding to the moire pattern is a peak frequency in an analyzed spatial frequency distribution.

10. The X-ray diagnostic apparatus according to claim 8, wherein said moire correction data generation circuit generates moire correction data including a plurality of moire fringes having said specified spatial frequency.

11. The X-ray diagnostic apparatus according to claim 8, wherein said moire correction data generation circuit generates a one dimensional original image signal from image data outputted from said X-ray detector and subjects said one dimensional original image signal to frequency analysis.

12. The X-ray diagnostic apparatus according to claim 8, wherein said moire correction data generation circuit generates a plurality of one dimensional original image signals corresponding to a plurality of directions from image data outputted from said X-ray detector, individually performs frequency analysis of a plurality of said one dimensional original image signals, specifies a plurality of peak frequencies corresponding to said one dimensional original image signals respectively, and selects a highest peak frequency from a plurality of said peak frequencies.

13. The X-ray diagnostic apparatus according to claim 12, wherein said moire correction data generation circuit generates moire correction data including a plurality of moire fringes having said selected highest peak frequency as a spatial frequency in a direction corresponding to said selected highest peak frequency.

14. The X-ray diagnostic apparatus according to claim 8, wherein said X-ray detector is a flat panel type detector adopting a direct conversion system or an indirect conversion system.

15. An X-ray diagnostic apparatus comprising:
an X-ray tube;
an X-ray detector;
a grid arranged on an image reception plane of said X-ray detector;
an arm configured to support said X-ray tube and said X-ray detector in such a manner that a distance between said X-ray tube and said image reception plane of said X-ray detector can be changed;
an arm support device configured to support said arm in such a manner that an angle of said arm can be changed;
a frequency analysis circuit configured to subject image data outputted from said X-ray detector to frequency analysis and specify a spatial frequency corresponding to a moire pattern; and
a moire correction circuit configured to attenuate a component of said specified spatial frequency included in image data outputted from said X-ray detector.

16. The X-ray diagnostic apparatus according to claim 15, wherein the spatial frequency corresponding to the moire pattern is a peak frequency in an analyzed spatial frequency distribution.

17. The X-ray diagnostic apparatus according to claim 15, wherein said frequency analysis circuit generates a one dimensional original image signal from image data outputted from said X-ray detector and subjects said one dimensional original image signal to frequency analysis.

18. The X-ray diagnostic apparatus according to claim 15, wherein said frequency analysis circuit generates a plurality of one dimensional original image signals corresponding to a plurality of directions from image data outputted from said X-ray detector, individually subjects a plurality of said primary image signals to frequency analysis, specifies a plurality of peak frequencies, and selects a highest peak frequency from a plurality of said peak frequencies.

19. X-ray diagnostic apparatus according to claim 18, wherein said moire correction circuit attenuates a spatial frequency component of said selected highest peak frequency in a direction corresponding to said selected highest peak frequency.

20. The X-ray diagnostic apparatus according to claim 15, wherein said X-ray detector is a flat panel type detector adopting a direct conversion system or an indirect conversion system.

21. An X-ray diagnostic apparatus comprising:
an X-ray tube;
an X-ray detector;
a grid arranged on an image reception plane of said X-ray detector;
an arm configured to support said X-ray tube and said X-ray detector in such a manner that a distance between said X-ray tube and said image reception plane of said X-ray detector can be changed;
a sensor configured to detect a distance between said X-ray tube and said image reception plane of said X-ray detector;

an arm support device configured to support said arm in such a manner that an angle of said arm can be changed;

a storage device configured to store moire image data when a distance between said X-ray tube and said image reception plane of said X-ray detector is a reference distance;

a moire image enlargement circuit which is configured to enlarge said moire image data based on said distance detected by said sensor and said reference distance; and a moire correction circuit which corrects image data outputted from said X-ray detector based on said enlarged moire image data.

22. An X-ray diagnostic apparatus according to claim 21, wherein said moire image enlargement circuit enlarges said moire image data in accordance with a magnification C1/C0 represented by the following expression:

$$C1/C0=(Pp-Pg)/((Pp/M1)-Pg)$$

where C0 is a pattern cycle of moire fringes corresponding to said reference distance;

C1 is a pattern cycle of moire fringes corresponding to said distance detected by said sensor;

Pp is a pixel pitch of said X-ray detector;

Pg is a grid plate projected image of said grid on said image reception plane of said detector corresponding to said reference distance; and M1 is a ratio of a magnification of a grid projected image on said image reception plane of said detector with respect to said grid corresponding to said reference distance and a magnification of a grid projected image on said image reception plane of said detector with respect to said grid corresponding to said distance detected by said sensor.

23. The X-ray diagnostic apparatus according to claim 22, wherein said moire image enlargement circuit calculates said ratio M1 in accordance with the following expression:

$$M1=(S1/(S1-D0))/(S0/(S0-D0))$$

where D0 is a physical distance between said grid and said image reception plane of said detector;

S0 is said reference distance; and

S1 is a distance detected by said sensor.

24. The X-ray diagnostic apparatus according to claim 21, wherein said X-ray detector is a flat panel type detector adopting a direct conversion system or an indirect conversion system.

* * * * *